United States Patent [19]
Hohlfeld et al.

[11] Patent Number: 5,902,252
[45] Date of Patent: May 11, 1999

[54] DEVICE AND PROCESS FOR MEASURING ACOUSTIC REFLECTANCE

[75] Inventors: Robert G. Hohlfeld, Arlington; Geoffrey Jenkins, Wellesley, both of Mass.

[73] Assignee: MDI Instruments, Inc., Woburn, Mass.

[21] Appl. No.: 09/012,695

[22] Filed: Jan. 23, 1998

[51] Int. Cl.[6] .................................................. A61B 5/12
[52] U.S. Cl. ........................................... 600/559; 73/585
[58] Field of Search ............................ 73/585, 587, 589; 600/559

[56] References Cited

U.S. PATENT DOCUMENTS

| | | | |
|---|---|---|---|
| 4,601,295 | 7/1986 | Teele | 73/585 |
| 5,594,174 | 1/1997 | Keefe | 600/559 |
| 5,699,809 | 12/1997 | Combs et al. | 600/559 |
| 5,792,072 | 8/1998 | Keefe | 600/559 |

*Primary Examiner*—Max Hindenburg
*Attorney, Agent, or Firm*—Wolf, Greenfield & Sacks, P.C.

[57] ABSTRACT

A device and a process for analysis of acoustic reflectance directs acoustic energy for a range of frequencies including resonance frequencies of the object being analyzed. The device detects waves reflected by the object to produce what is called an acoustic reflectance curve. The electronic signal applied to an acoustic transducer at each frequency is gradually increased in amplitude to a desired amplitude. After applying the signal for a period of time at the desired amplitude, the amplitude is gradually decreased. This technique reduces noise that would otherwise occur if a signal of the desired amplitude was applied directly. The signal applied to the acoustic transducer also may be scaled according to a measured response of the device to open air, i.e., without any expected reflectance. Normalizing the signal applied to the acoustic transducer rather than the signal received from a microphone increases the dynamic range of the device. The device also may require operation for several sweeps through a range of incident frequencies in order to ensure proper user technique is used. When the data for the several sweeps is analyzed, the best result of the several sweeps may be stored as the output.

10 Claims, 5 Drawing Sheets

DEVICE AND PROCESS FOR MEASURING ACOUSTIC REFLECTANCE

FIELD OF THE INVENTION

The present invention relates generally to devices and processes which provide information about a bodily cavity based on a measured response to acoustic excitation. More particularly, the invention relates to devices and processes which involve measuring acoustic reflectance of components of the ear.

BACKGROUND OF THE INVENTION

Many of the problems with common diagnostic techniques for ear pathologies were overcome by a device which measures acoustic reflectance, which is a quantity related to the complex acoustic impedance of the middle ear. Acoustic reflectance also is used to analyze the nasal cavity or to measure volume of the lungs. This technology also may be used for veterinary purposes.

Acoustic reflectometry for the ear involves transmitting sound waves (called incident waves) through the ear canal to the tympanic membrane. The incident waves are selected from a range of frequencies including the resonance frequency of the tympanic membrane; ideally the amplitudes of the incident waves also are the same for all frequencies, but this result often is not achievable. Some of the incident waves are reflected off the tympanic membrane and other components of the ear. The reflected waves may be detected by a microphone. In order to detect resonance, the microphone detects the vector sum of the incident and reflected waves over the range of frequencies. The envelope of this vector sum, herein called an acoustic reflectance curve, has a dip, also called a null. In the literature, this diagnostic technique is generally referred to as acoustic reflectometry or acoustic otoscopy and the device is generally referred to as an acoustic reflectometer or acoustic otoscope.

A suitable device and methodology for measuring acoustic reflectance of an ear are described in U.S. Pat. Nos. 4,601,295 and 4,459,966 to John H. Teele (the Teele patents). Such devices were made commercially available by ENT Medical Devices, Inc., of Wareham, Mass., and Endeco, Inc., of Marion, Mass. With these devices, the amplitude of a peak of the null of the acoustic reflectance curve, called the null value, was the primary basis for diagnosis of ear pathologies. It was discovered that the accuracy of the measurement of the null value obtained with an acoustic reflectometer depended on the line of sight from the instrument tip to the tympanic membrane. This problem was overcome by analyzing the shape of the acoustic reflectance curve, as shown in PCT Publication WO96/23293 and U.S. Pat. No. 5,699,809 (Combs et al.).

Another kind of acoustic reflectance measurement is shown in U.S. Pat. Nos. 5,594,174 and 5,651,351, to Douglas Keefe. These patents disclose a circuit that detects reflected waves separately from the incident waves. This separation permits the transfer function of the ear canal to be determined.

The accuracy of measurements of acoustic reflectance may be diminished due to noise. Noise may be caused, for example, by the response of an acoustic chamber to a change in frequency of the acoustic wave exciting the chamber or by noise in the received signal. In addition, normalization of the device by adjusting the received signals to compensate for the frequency response of the device limits the dynamic range which may be measured by the device. Finally, results may be unreliable due to user technique, particularly if the operator does not operate the device for a sufficient period of time to collect a sufficient amount of data for analysis. The present invention overcomes these difficulties to improve the sensitivity and reliable of the device.

SUMMARY OF THE INVENTION

A device and a process for analysis of acoustic reflectance directs acoustic energy for a range of frequencies including resonance frequencies of the object being analyzed. The device detects waves reflected by the object to produce what is called an acoustic reflectance curve. The electronic signal applied to an acoustic transducer at each frequency is gradually increased in amplitude to a desired amplitude. After applying the signal for a period of time at the desired amplitude, the amplitude is gradually decreased. This technique reduces noise that would otherwise occur if a signal of the desired amplitude was applied directly. The signal applied to the acoustic transducer also may be scaled according to a measured response of the device to open air, i.e., without any expected reflectance. Normalizing the signal applied to the acoustic transducer rather than the signal received from a microphone increases the dynamic range of the device. The device also may require operation for several sweeps through a range of incident frequencies in order to ensure proper user technique is used. When the data for the several sweeps is analyzed, the best result of the several sweeps may be stored as the output.

In one aspect, a method for generating an acoustic signal, in an acoustic wave guide, involves applying an electrical signal to an acoustic transducer in the waveguide. For each of a plurality of frequencies, the electrical signal is applied over a first period of time while increasing the amplitude of the signal from a first amplitude to a second amplitude higher than the first amplitude. The electrical signal is applied using the second amplitude for a second period of time after the first period of time. The electrical signal is applied over a third period of time after the second period of time, while decreasing the amplitude of the signal from the second amplitude to a third amplitude lower than the second amplitude. In one embodiment the amplitude of the signal may be scaled according to reflectance from open air into the acoustic waveguide at each selected frequency. In another embodiment, the incident and reflected acoustic signals may be sensed over a period of time starting after the beginning of the second period of time and ending before the end of the second period of time.

In another aspect, a method for generating an acoustic signal, in an acoustic wave guide, involves applying an electrical signal to an acoustic transducer in the waveguide. An initial desired amplitude is generated and the amplitude is scaled according to reflectance from open air into the acoustic waveguide at each selected frequency. An electrical signal with the scaled amplitude is applied to the acoustic transducer.

In another aspect, a method for generating an acoustic signal, in an acoustic wave guide, involves applying an electrical signal to an acoustic transducer in the waveguide. A set of sweeps over a range of frequencies is performed so long as a control is activated. When at least four sweeps have occurred, a result is output. When less than four sweeps have occurred, it is assured that the data collected is insufficient for reliable analysis and a user error has occurred. Such an error may be indicated to the user.

DETAILED DESCRIPTION

The present invention will be more completely understood through the following detailed description which should be read in conjunction with the attached drawing in which similar reference numbers indicate similar structures. The description incorporates by reference the descriptions of acoustic reflectometry found in U.S. Pat. Nos. 4,601,295 and 4,459,966 (Teele) and U.S. Pat. No. 5,699,809 (Combs et al.).

One process for measuring acoustic reflectance of a human ear will be described in connection with FIGS. 1–2. It should be understood that the same principles may be applied to other bodily cavities, such as the nasal cavity and the lungs. Such a device also may be used for veterinary purposes.

Figure 1:
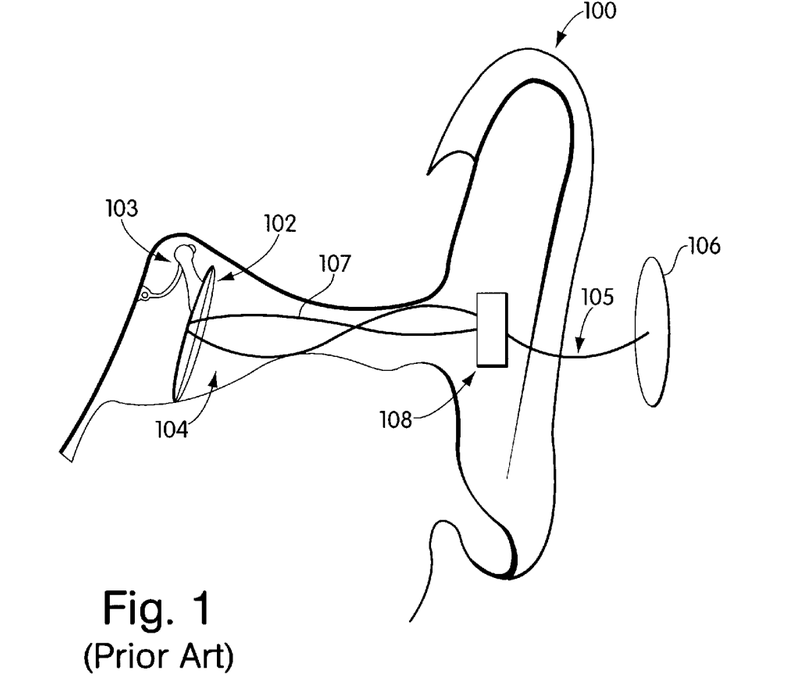
FIG. 1 is a cross sectional diagram of an ear illustrating the principle of acoustic reflectance applied to a normal ear.

FIG. 1 shows a typical ear 100 having a tympanic membrane (an ear drum) 102, an ear canal 104, and middle ear 103. To measure acoustic reflectance of the ear, a low amplitude tone at a given frequency, indicated by line 105, is generated by an acoustic transducer, shown schematically at 106. The acoustic transducer generates sound waves for several frequencies, typically in the range of 500 hertz to 20 kilohertz. The low amplitude sound wave enters the ear canal and is incident on the ear drum 102. This sound wave is absorbed in part and reflected in part by the ear structures, including the tympanic membrane, osicles, middle ear cleft and other components of the middle ear. The amplitude and phase of the reflected sound waves from these components are a function of the test frequency used and the complex acoustic impedance of the ear structures. In a healthy ear, some minimal reflection from the tympanic membrane and middle ear is expected. The complex acoustic impedance of the middle ear, in turn, depends very strongly on the conditions within the middle ear, and in particular on whether there is effusion, such as fluid, or abnormal pressure present within the middle ear. The vibration of a normal ear drum absorbs approximately half of the incident waves, resulting in weak reflected waves indicated by a line 107. A microphone 108 receives both the incident wave 105, the reflected wave 107 and reflected waves from ear components and as a result obtains a vector sum of the values. With appropriate circuitry, the reflected signal may be identified separately from the incident signal.

Figure 2:
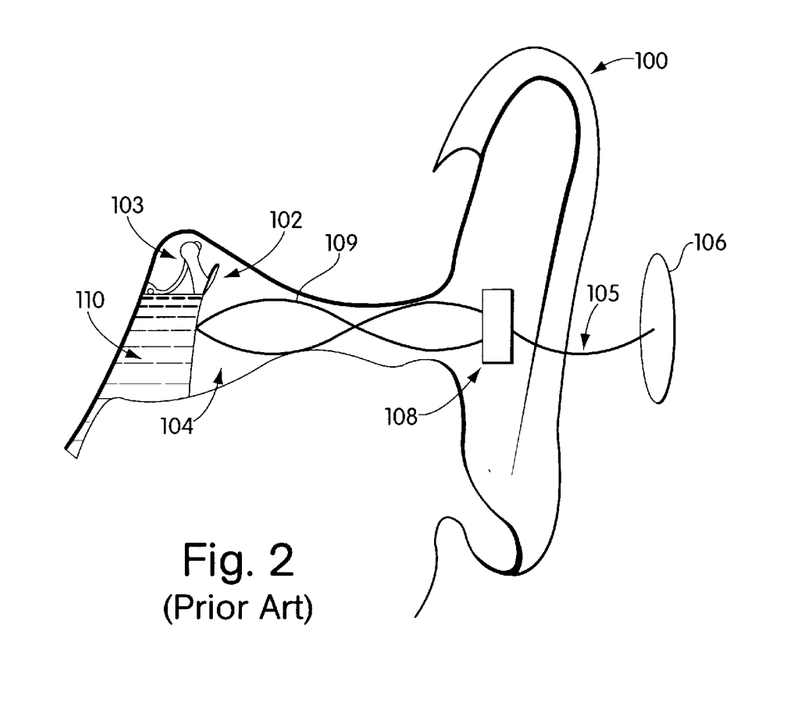
FIG. 2 is a cross sectional diagram of an ear illustrating the principle of acoustic reflectance as applied to an ear with an effusion.

Referring now to FIG. 2, an ear 100 is shown to have effusion 110. The middle ear effusion limits ear drum vibration which causes large reflected waves as indicated at 109. The envelope of a vector sum of incident waves 105 and reflected waves 109 has a null at the quarter wave length points.

The accuracy of measurements and analysis of the reflected signal may be improved using several techniques described herein. First, noise caused by the response of the acoustic transducer and the device to a change in the frequency of the acoustic signal being generated is reduced by gradually increasing the amplitude of the signal exciting the transducer. The dynamic range of the device also may be improved by normalizing the device by adjusting the amplitude of the incident signal to compensate for the frequency response of the server. The effects of user technique on the reliability of results may be reduced by requiring a minimum number of successive tests using the device. These techniques improve the sensitivity and specificity and reliability of the device.

Figure 3:
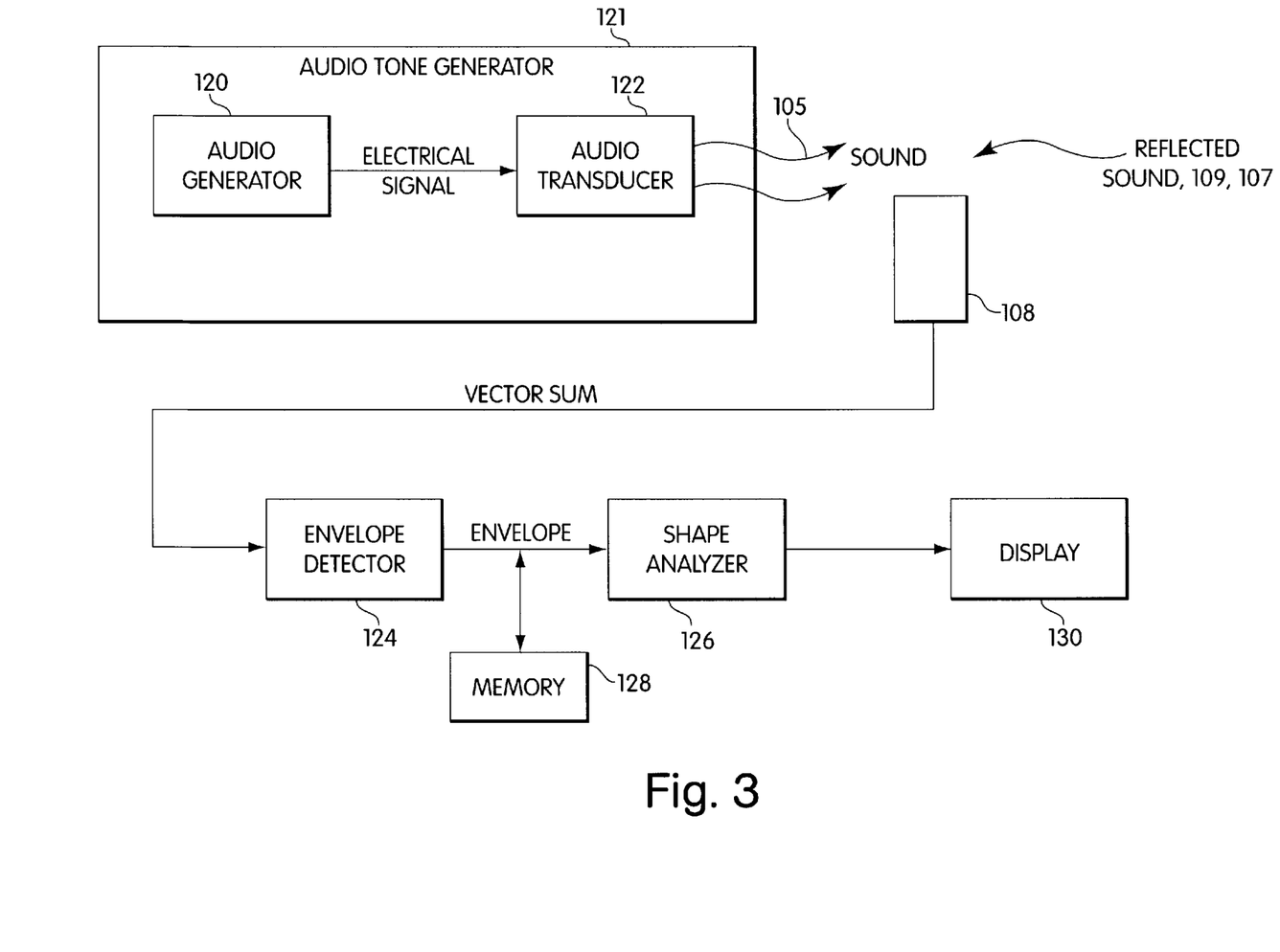
FIG. 3 is a block diagram describing a system in accordance with the present invention.

Electronic circuitry in one embodiment of the present invention will now be described in connection with FIG. 3. In FIG. 3, an audio tone generator 121 includes an audio generator 120, described in more detail below, which produces an electrical signal which is applied to an audio transducer 122. The audio transducer, in response to the electrical signal, generates a low level acoustic sound wave (105 in FIGS. 1 and 2) which is applied to the outer ear canal. The audio transducer 122 may be an electronic earphone, electromagnetic earphone, or other type of transducer. The transducer may be a small loudspeaker such as used in high fidelity sound headsets.

A portion of the incident sound wave is reflected by ear structures as described above. These reflected waves are summed with an incident wave by microphone 108. The microphone may be a condenser microphone, an electrostatic microphone, piezoelectric device or other kind of microphone. The signal output by the microphone represents the vector sum of the incident wave and the reflected sound waves, having a voltage which is inversely proportional to the amplitude of the reflected waves.

An envelope detector 124 samples and converts the vector sum represented by the signal output by the microphone to an envelope signal represented by a voltage which varies with the frequency of the incident wave. The envelope detector 124 may be implemented as a peak value envelope detector, a root-mean square (RMS) voltage detector, or analog-to-digital converter, or by using information about the frequency spectrum. The envelope so detected is called herein an acoustic reflectance curve.

A shape analyzer 126 electronically measures the shape of a region of the acoustic reflectance curve to obtain an indicator of ear condition which is substantially independent of the line of sight from a sound source to the tympanic membrane. This information may be a measure of the rate of change of acoustic reflectance with respect to a change in frequency around the null, on either side of the null or on a region of the curve or of the entire curve. This measure may be an angle, gradient, slope, width, or other measure of the shape of the acoustic reflectance curve. This information is then displayed in a suitable format by a display 130.

In FIG. 3, a memory 128 may be used to store data representing acoustic reflectance curves. With such a memory, the circuit may be operated to perform automatically a number of sequential tests on the ear. The best result among the tests may be kept and the others may be discarded. For example, the best result could be defined as the measurement of the shape of the acoustic reflectance curve having the deepest null value. The device also may require a minimum number of sweeps in order to provide a valid output. For example, at least four sweeps may be required. A user error may be presumed to have occurred if the minimum number of sweeps is not performed. Such an error may be indicated, for example, by flashing on a display.

Having now described the general arrangement of a circuit in one embodiment of the invention, the audio generator 120 will now be described in more detail. The audio generator produces a sequence of discrete frequencies, typically within the range of 500 to 20,000 Hz. In one embodiment, the sequence includes forty-four frequencies between 1801 Hz and 4464 Hz, as listed in Table 1, to generate the measurement of acoustic reflectance as a function of frequency. Any other range of frequencies that demonstrates the responses of the ear to an acoustic signal that may vary due to physiological condition. The instrument scans through the sequence of frequencies, e.g., in increasing frequency order, to generate a "sweep" with a duration of approximately 0.2 seconds.

TABLE 1

| Freq. No. | Hz | Freq. No. | Hz | Freq. No. | Hz | Freq. No. | Hz |
|---|---|---|---|---|---|---|---|
| 1 | 1,301 | 12 | 2,583 | 23 | 3,222 | 34 | 3,853 |
| 2 | 1,997 | 13 | 2,637 | 24 | 3,289 | 35 | 3,931 |
| 3 | 2,056 | 14 | 2,694 | 25 | 3,342 | 36 | 3,981 |
| 4 | 2,119 | 15 | 2,753 | 26 | 3,397 | 37 | 4,032 |
| 5 | 2,178 | 16 | 2,815 | 27 | 3,453 | 38 | 4,085 |
| 6 | 2,232 | 17 | 2,880 | 28 | 3,511 | 39 | 4,167 |
| 7 | 2,289 | 18 | 2,934 | 29 | 3,571 | 40 | 4,223 |
| 8 | 2,350 | 19 | 2,990 | 30 | 3,634 | 41 | 4,281 |
| 9 | 2,404 | 20 | 3,049 | 31 | 3,698 | 42 | 4,340 |
| 10 | 2,470 | 21 | 3,109 | 32 | 3,743 | 43 | 4,401 |
| 11 | 2,520 | 22 | 3,173 | 33 | 3,811 | 44 | 4,464 |

Figure 4:
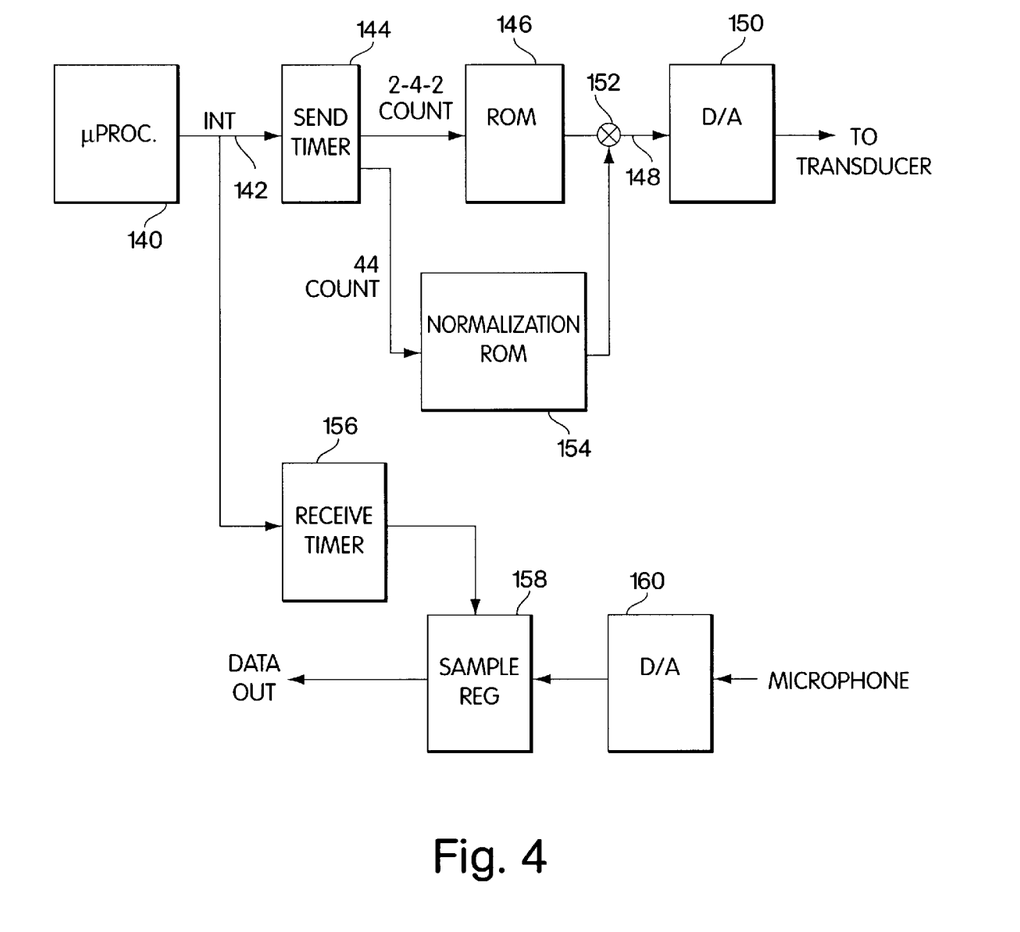
FIG. 4 is a more detailed block diagram of the audio generator of FIG. 3.

FIG. 4 illustrates in more detail one embodiment of the audio generator 120, which also provides control to the envelope detector 124. The audio generator 120 includes a microprocessor 140 which, according to the desired frequency of the electrical signal to be applied to the audio transducer 122, generates an interrupt, indicated at 42, for each sample of the signal to be generated. Accordingly, the processor generates interrupts occurring at a rate of some factor, e.g., eight, times the selected frequency. A send timer 144 receives the interrupts 42 to generate addresses to a read-only memory (ROM) 146 which stores samples of a single cycle of a sine wave. The ROM 146 implements a lookup table which, according to the input address, outputs one of the sample values of the electrical signal in digital form, as indicated at 148. The signal 148 is applied to a digital to analog (D/A) converter 150 to generate the electrical signal applied to the audio transducer 122. As will be discussed in more detail below, the signal 148 may be normalized, as indicated at 152, by scaling the signal 148 according to output of a normalization memory 154 which also receives information from the timer 144. The interrupt 142 also is applied to a receive timer 156 which controls a sample register 158 connected to an analog to digital (A/D) converter 160 which receives an analog signal from the microphone 108.

In this embodiment, the digital-to-analog converter 150 used to transmit the sound waves has an 8-bit input and is a unipolar device. Therefore the mean signal value of the sine wave output by this D/A converter 150 is 128 and the sine wave is represented by the following mathematical formula:

$$x_i = \text{floor}\left(A \cdot \sin\left(2 \cdot \pi \cdot \frac{i}{8}\right) + 128.5\right)$$

where i=0.7, and A=100, yielding values $$x^T = (128\ 199\ 228\ 199\ 128\ 57\ 28\ 57)$$

Figure 5:
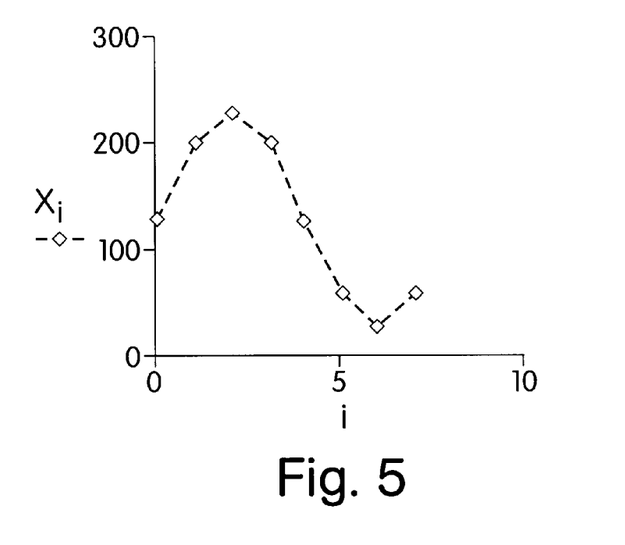
FIG. 5 is a graph illustrating eight samples of a sine wave used to generate an electrical signal to be applied to the acoustic transducer.

These samples are stored in the ROM 146. A sample plot (see FIG. 5) shows the resulting sampling of the sine wave generated.

As noted above, one of the timers in the microprocessor 140 generates the interrupts 42 at some factor times the desired frequency. For example, if the desired frequency is 2500 Hz, the interval between interrupts is:

$$\frac{1 \cdot \sec}{8 \cdot 2500} = 5 \cdot 10^{-5} \cdot \sec$$

This period also defines the time interval for data collection, since the same interrupts 42 are used for data acquisition. At each interrupt, the next entry in the sine wave output from ROM 146 is sent to the D/A converter 150, wrapping back to the first entry at the completion of a cycle of the sine wave.

Figure 6:
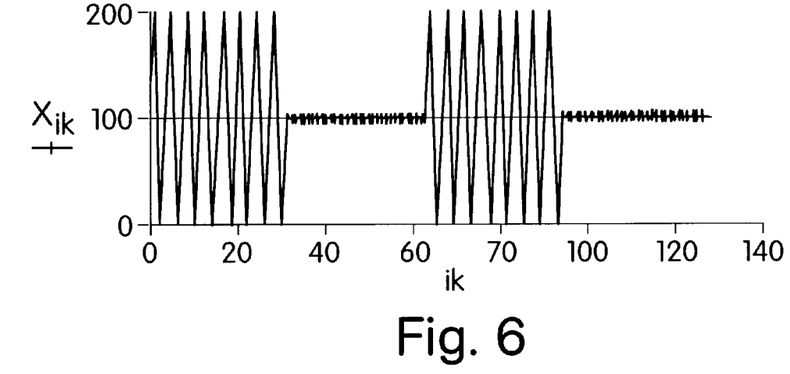
FIG. 6 is a graph illustrating the output of the acoustic transducer for two frequencies.

The microprocessor 140 causes a burst of a number, e.g., thirteen, of integral sine wave cycles at each frequency to be output. The microprocessor allows a number, e.g., two, of periods defined by the same frequency, either prior to or after the burst, to pass before continuing to the next entry in the frequency table. The first ten cycles may be used to stabilize the acoustic transducer at the selected frequency, and three additional cycles can be used for during which the output of the microphone may be sampled. The microprocessor 140 generates the interrupts for all of the desired frequencies of a sweep. The entire sweep thus appears as a sequence of bursts of integral numbers of sine waves of increasing frequency as illustrated in FIG. 6. The microprocessor 140 may determine whether at least four sweeps are made during the period of time that a user has pressed an input button.

Figure 7:
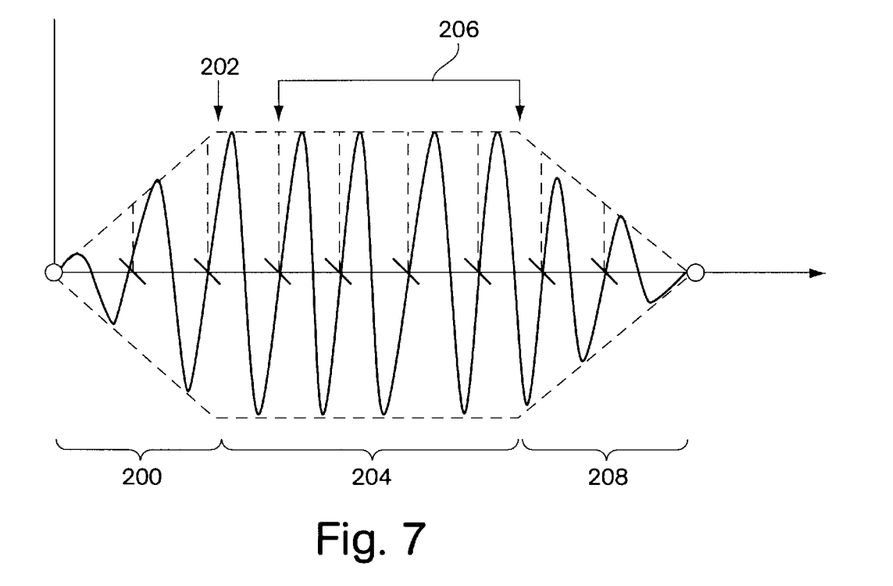
FIG. 7 is a graph illustrating how a signal at a given frequency is gradually increased and then gradually decreased in amplitude in one embodiment of the invention.

The amplitude of the sine wave generated at each frequency also may be scaled over time as shown in FIG. 7. First, during a first time period 200 the average amplitude may gradually increase from zero to the desired amplitude indicated at 202. This first time period may be, for example, two cycles long. For a second time period, as indicated at 204, the output signal may be at the desired amplitude. This second time period 204 may be, for example, four cycles long. Sampling of the data from the microphone may occur during the last few cycles, e.g. the last three, of second time period 204 as indicated at 206. Finally, the pulse may end with a third time period 208 during which the amplitude of the output signal gradually decreases from the desired amplitude 202 to zero. This third time period 208 may be, for example, two cycles long.

Having now described the generation of a signal to be applied to the acoustic transducer, the acquisition of a signal from the microphone will now be described. The signal acquired from the microphone 108 is a superposition of the transmitted signal and the signal reflected by the tympanic membrane. The microphone 108 is connected to an A/D converter 160 which generates a digital output for subsequent processing. Operation of the A/D converter 160 is keyed to the same interrupts which are used for the transmission of the acoustic signal. The sampled values generated by the A/D converter are digital values proportional to the instantaneous pressure at the microphone.

Data collection occurs over an integer number of cycles of the transmitted sine wave at each frequency. In one embodiment, thirteen cycles of the same amplitude are applied to the ear canal. Ten transmitted cycles may be allotted for the system to stabilize, and then data may be collected for three cycles of the transmitted wave. In the embodiment described in connection with FIG. 7, three cycles allow the device to stabilize at selected frequency, then data may be collected for three cycles. The remaining two cycles allow the device to stabilize to a non-visualizing condition. In both embodiments, several cycles, e.g., two, occur between each pulse at each frequency.

Given the signal output by the A/D converter 160, the envelope detector 124 measures the acoustic intensity to provide an acoustic reflectance curve. For this purpose a baseband detection technique may be used. For each frequency of the incident signal, the sampled values from the A/D converter are multiplied by sine and cosine (quadrature) waves at that frequency and summed over each cycle, which may be expressed mathematically by the following:

$$A(k) = \sum_n acq\_signal(n,k) \sin\left|\frac{n}{o}\right|;$$

$$\text{and } B(k) = \sum_n acq\_signal(n,k) \cos\left|\frac{n}{o}\right|,$$

where, acq_signal(n,k) represents the nth sampled value at the kth frequency for a given cycle. The arguments (n/8) of the trigonometric terms reflect the fact that eight samples are taken per cycle. In practice, the values of trigonometric functions are not computed during evaluation of A(k) and B(k), but rather lookup table values are used, as is done for the generation of the incident wave by the audio generator. It is possible to average the values obtained for A(k) and B(k) for the cycles during which sampling occurs for each frequency.

Given the values of A(k) and B(k), the power P(k) present in the fundamental frequency of the output from the A/D converter 160 may be represented as:

$$P(k) = A(k)^2 + B(k)^2$$

Reduction of the normalized phase quadrature detected power to acoustic intensity is accomplished by taking the square root of the power P(k). The graph of the square root of the power P(k) for all k is the acoustic reflectance curve. The computation of the square root of the power P(k) may be performed by table lookup.

The measured power P(k) may be normalized, prior to computing its square root, to account for nonlinearities and to remove frequency dependence in the response of the acoustic assembly (acoustic chamber, microphone and speaker) from which the signal is obtained. This normalization is based on an assumption that if the incident waves were applied to open air, there should be no measured reflection. Thus, the envelope of the vector sum output by the microphone, i.e., the acoustic reflectance curve, should be flat when the incident wave are directed into open air. However, due to nonlinearities in the acoustic system, the acoustic reflectance curve in response of the device to open air typically is not flat.

Figure 8A:
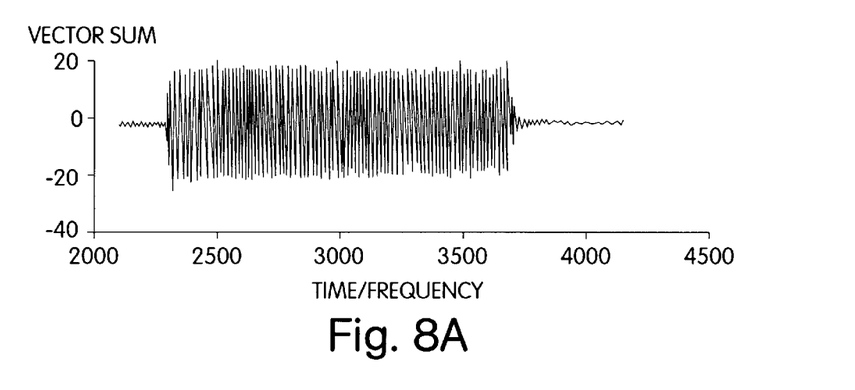
FIG. 8A represent the vector sum of the reflectance from open air using a device in accordance with the invention.
Figure 8B:
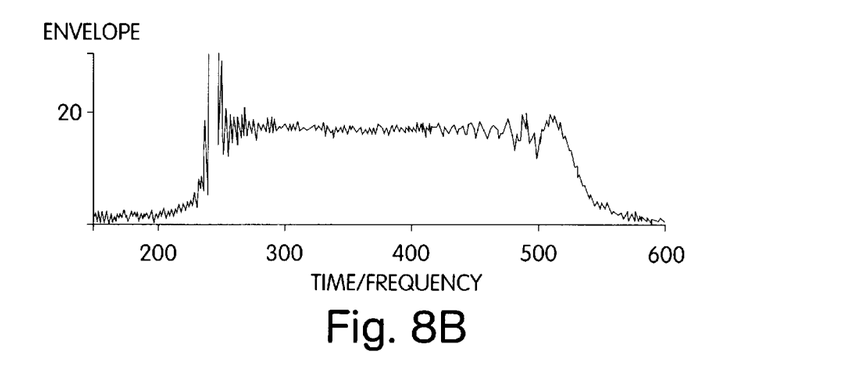
FIG. 8B represent the corresponding envelope of the reflectance from open air using a device in accordance with the invention.

For example, an actual vector sum obtained with a device using a continuous sweep audio tone generator as applied to open air is shown in FIG. 8A. In FIG. 8A, the abscissa represents either increasing time or the frequency of the incident wave in arbitrary units. The ordinate represents the amplitude of the vector sum output by the microphone in arbitrary units. In FIG. 8B, the abscissa represents increasing time or frequency of the incident wave in arbitrary units. The ordinate represents the magnitude of the envelope in arbitrary units. There are noticeable irregularities in the envelope shown in FIG. 8B.

The process of acoustic assembly normalization is intended to characterize the frequency response of the acoustic system so that the frequency variation of the reflected sound energy from the tympanic membrane can be measured independently of the frequency response of the instrument. The frequency variation of the acoustic system may be measured by recording the response of the instrument operating in open air for a series of sweeps.

For each sweep, the power P(k) measured for all frequencies k is determined as described above. In one embodiment, using the power P(k) for a given frequency k, a normalization constant may be calculated for the frequency in the following manner. The minimum power, min(P(k)), obtained for any frequency is identified. A normalization constant, Norm(k), is then computed for each frequency k such that, when the device is operated in open air, the values of P(k) for all k are adjusted to a value S, e.g., 255, corresponding to the maximum squared sampled value. Such normalization constants for each frequency may be computed according to the following equation:

$$\text{Norm}(k) := \frac{S \min(P(k))}{P(k)}.$$

This normalization constant Norm(k) is used to scale the power P(k) measured for a given frequency k prior to the computation of the square root of P(k).

Error checking may be performed during normalization to ensure that the acoustic assembly is performing within expected tolerances. The expected range of performance of the acoustic assembly is a factor of two in sound amplitude (pressure) during normalization, or a factor of four in power. The normalization routine may verify that the minimum power measured in the range of channels is greater than ¼ of the maximum power measured in the range of channels, or otherwise indicate an error. Such a test is represented by the following equation:

$$\min(P(k)) > \frac{1}{4}\max(P(k)).$$

The set of normalization constants so determined may be written into a nonvolatile memory on the device. These normalization constants may be permanent for a device and may be set when the device is manufactured. Alternatively, while the device could be designed to allow a user to periodic set the device.

Normalization also may be performed by adjusting the amplitude of the incident signal created by the audio generator, rather than by adjusting the output of the A/D converter. By performing normalization by adjusting the amplitude of the incident signal, the maximum dynamic range of the A/D converter may be utilized, thereby allowing less sensitive, and thus less costly, devices to be used for the transducer and microphone and improving the results of analysis of the measurement made by the device. Adjusting the incident signal may be performed by scaling the amplitude of the intended incident signal using a multiplicative constant. One way to determine the multiplicative constant for a given frequency k involves using the normalization constant Norm(k) and the following equation: $\sqrt{1}(\text{Norm}(k))$.

This value is used to scale the voltage applied to the D/A converter so that the resulting signal received by the A/D converter is substantially constant over all frequencies when the device is directed to open air.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention as defined by the appended claims.

What is claimed is:

1. A method for generating an acoustic signal, in an acoustic wave guide, by applying an electrical signal to an acoustic transducer in the waveguide, comprising the steps of, for each of a plurality of frequencies:

applying the electrical signal over a first period of time while increasing the amplitude of the signal from a first amplitude to a second amplitude higher than the first amplitude;

applying the electrical signal using the second amplitude for a second period of time after the first period of time; and applying the electrical signal over a third period of time after the second period of time, while decreasing the amplitude of the signal from the second amplitude to a third amplitude lower than the second amplitude.

2. The method of claim 1, further comprising the step of:

scaling the amplitude according to reflectance from open air into the acoustic waveguide at each selected frequency.

3. The method of claim 1, further comprising:

sensing the incident and reflected acoustic signals over a period of time starting after the beginning of the second period of time and ending before the end of the second period of time.

4. A method for generating an acoustic signal, in an acoustic wave guide, by applying an electrical signal to an acoustic transducer in the waveguide, comprising the steps of:

generating an initial desired amplitude;

scaling the amplitude according to reflectance from open air into the acoustic waveguide at each selected frequency;

applying an electrical signal with the scaled amplitude to the acoustic transducer.

5. A method for generating an acoustic signal, in an acoustic wave guide, by applying an electrical signal to an acoustic transducer in the waveguide, comprising the steps of:

performing a set of sweeps over a range of frequencies so long as a control is activated;

when at least four sweeps have occurred, outputting a result; and when less than four sweeps have occurred, determining that an error has occurred.

6. A device for generating an acoustic signal, in an acoustic wave guide, by applying an electrical signal to an acoustic transducer in the waveguide for each of a plurality of frequencies, the device comprising:

means for applying the electrical signal over a first period of time while increasing the amplitude of the signal from a first amplitude to a second amplitude higher than the first amplitude;

means for applying the electrical signal using the second amplitude for a second period of time after the first period of time; and means for applying the electrical signal over a third period of time after the second period of time, while decreasing the amplitude of the signal from the second amplitude to a third amplitude lower than the second amplitude.

7. The device of claim 6, further comprising:

means for scaling the amplitude according to reflectance from open air into the acoustic waveguide at each selected frequency.

8. The device of claim 6, further comprising:

means for sensing the incident and reflected acoustic signals over a period of time starting after the beginning of the second period of time and ending before the end of the second period of time.

9. A device for generating an acoustic signal, in an acoustic wave guide, by applying an electrical signal to an acoustic transducer in the waveguide, comprising:

means for generating an initial desired amplitude;

means for scaling the amplitude according to reflectance from open air into the acoustic waveguide at each selected frequency;

means for applying an electrical signal with the scaled amplitude to the acoustic transducer.

10. A device for generating an acoustic signal, in an acoustic wave guide, by applying an electrical signal to an acoustic transducer in the waveguide, comprising:

means for performing a set of sweeps over a range of frequencies so long as a control is activated;

means, operative when at least four sweeps have occurred, for outputting a result; and means, operative when less than four sweeps have occurred, for determining that an error has occurred.

* * * * *